United States Patent [19]

Starzl et al.

[11] Patent Number: 5,348,966
[45] Date of Patent: Sep. 20, 1994

[54] METHOD FOR TREATING PYODERMA AND SEZARY'S SYNDROME USING FK 506 AND RELATED COMPOUNDS

[75] Inventors: Thomas E. Starzl; Satoru Todo, both of Pittsburgh, Pa.

[73] Assignee: Fujisawa Pharmaceutical Co., Ltd., Osaka, Japan

[21] Appl. No.: 155,533

[22] Filed: Nov. 22, 1993

Related U.S. Application Data

[63] Continuation of Ser. No. 15,880, Feb. 10, 1993, abandoned, which is a continuation of Ser. No. 899,945, Jun. 17, 1992, abandoned, which is a continuation of Ser. No. 602,638, Oct. 24, 1990, abandoned.

[51] Int. Cl.$^5$ .................. A61K 31/445; A61K 31/33; A61K 31/40
[52] U.S. Cl. .................. 514/326; 514/183; 514/191; 514/411; 514/422
[58] Field of Search .................. 514/326, 422

[56] References Cited

U.S. PATENT DOCUMENTS

| | | | |
|---|---|---|---|
| 3,244,592 | 4/1966 | Arai | 424/275 |
| 4,212,881 | 7/1980 | Sasaki et al. | 424/275 |
| 4,894,366 | 1/1990 | Okuhara et al. | 514/63 |
| 4,929,611 | 5/1990 | Okukara et al. | 514/183 |

FOREIGN PATENT DOCUMENTS

| | | |
|---|---|---|
| 0184162 | 6/1986 | European Pat. Off. . |
| 0315978 | 5/1989 | European Pat. Off. . |
| 0323042 | 7/1989 | European Pat. Off. . |

OTHER PUBLICATIONS

Arai et al, *J. Antibiotics*, vol. 15, pp. 231–232 (1962).
Swindells et al, *Can. J. Chem.*, vol. 56, pp. 2491–2492 (1978).
Findlay et al, *Can. J. Chem.*, vol. 58, pp. 579–590 (1980).
Tanaka et al, *J. Am. Chem. Soc.*, vol. 109, pp. 5031–5033 (1987).
*Chem. Abstracts*, 106:134814j (1987).
*Chem. Abstracts*, 107:236308k (1987).
*Chem. Abstracts*, 108:101198z (1988).
*Chem. Abstracts*, 109:170104y (1988).
*New York Times*, Oct. 18, 1989, pp. 1 and B7.

*Primary Examiner*—Marianne M. Cintins
*Assistant Examiner*—T. J. Criares
*Attorney, Agent, or Firm*—Oblon, Spivak, McClelland, Maier & Neustadt

[57] ABSTRACT

Administration of FK506 or related macrolide compounds is effective for the treatment of pyoderma and Sezary's syndrome.

15 Claims, No Drawings

METHOD FOR TREATING PYODERMA AND SEZARY'S SYNDROME USING FK 506 AND RELATED COMPOUNDS

This application is a continuation of application Ser. No. 08/015,880 filed on Feb. 10, 1993 now abandoned, which was a continuation of application Ser. No. 07/899,945, filed on Jun. 17, 1992, now abandoned which was a continuation of application Ser. No. 07/602,638, filed on Oct. 24, 1990, now abandoned.

BACKGROUND OF THE INVENTION

1. Field of the Invention

The present invention relates to the use of macrolide compounds, such as FK 506, for the treatment of pyoderma and Sezary's syndrome.

2. Discussion of the Background

Sezary's syndrome is a T-cell lymphoma which has a lethal course, usually over a 4 to 8 year period. The malignant T-lymphocytes infiltrate the skin and cause what is known as the "redman syndrome", but they also cause lymphnode enlargement. The T-lymphocytes represent nearly 100% of the circulating white cells.

Pyoderma gangrenosum is a skin disorder which is thought to be of autoimmune etiology. It causes skin ulceration and pustule formation, and these are profoundly deforming. Such patients have a greatly degraded quality of life, and there is high rate of suicide among the victims.

There are no highly effective ways of treating either sezary syndrome or pyoderma gangrenosum.

Accordingly, there remains a need for an effective method for the treatment of pyoderma. In addition, there remains a need for an effective method for the treatment of Sezary's syndrome.

SUMMARY OF THE INVENTION

Accordingly, one object of the present invention is to provide a method for treating pyoderma gangrenosum.

A further object is to provide a method for treating Sezary's syndrome.

These and other objects, which will become apparent during the following detailed description, have been achieved by the inventors' discovery that administration of an effective amount of a macrolide compound, such as FK 506, is an effective treatment of pyoderma gangrenosum and Sezary's syndrome.

DETAILED DESCRIPTION OF THE PREFERRED EMBODIMENTS

The macrolide compounds used in this invention can be represented by the following general formula (I).

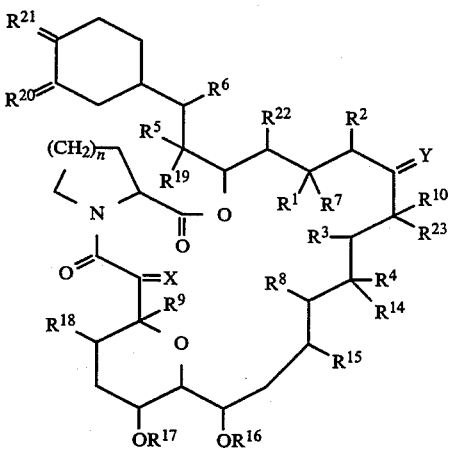

wherein each vicinal pair of substituents [$R^1$ and $R^2$], [$R^3$ and $R^4$], [$R^5$ and $R^6$] independently
a) represent two vicinal hydrogen atoms, or
b) form a second bond between the vicinal carbon atoms to which they are attached;

in addition to its significance above, $R^2$ may represent an alkyl group;

$R^7$ represents H, OH, protected hydroxy or O-alkyl, or in conjunction with $R^1$ it may represent =O;

$R^8$ and $R^9$ independently represent H or OH;

$R^{10}$ represents H, alkyl, alkyl substituted by one or more hydroxyl groups, alkenyl, alkenyl substituted by one or more hydroxyl groups, or alkyl substituted by =O;

X represents O, (H,OH), (H,H) or —$CH_2O$—;

Y represents O, (H,OH), (H,H), N—$NR^{11}R^{12}$ or N—$OR^{13}$;

$R^{11}$ and $R^{12}$ independently represent H, alkyl, aryl or tosyl;

$R^{13}$, $R^{14}$, $R^{15}$, $R^{16}$, $R^{17}$, $R^{18}$, $R^{19}$, $R^{22}$ and $R^{23}$ independently represent H or alkyl;

$R^{20}$ and $R^{21}$ independently represent O, or they may independently represent ($R^{20}$a,H) and ($R^{21}$a,H) respectively;

$R^{20}$a and $R^{21}$a independently represent OH, O-alkyl or $OCH_2OCH_2CH_2OCH_3$ or $R^{21}$a is protected hydroxy;

in addition, $R^{20}$a and $R^{21}$a may together represent an oxygen atom in an epoxide ring;

n is 1, 2 or 3;

in addition to their significances above, Y, $R^{10}$ and $R^{23}$, together with the carbon atoms to which they are attached, may represent a 5- or 6-membered N-, S- or O- containing heterocyclic ring, which may be saturated or unsaturated, and which may be substituted by one or more groups selected from alkyl, hydroxy, alkyl substituted by one or more hydroxyl groups, O-alkyl, benzyl and —$CH_2Se(C_6H_5)$; and pharmaceutically acceptable derivatives thereof.

The term "lower" used in the specification is intended to mean 1 to 6 carbon atoms, unless otherwise indicated.

Suitable "alkyl" means straight or branched saturated aliphatic hydrocarbon residue and may include lower alkyl such as methyl, ethyl, propyl, isopropyl, butyl, isobutyl, pentyl, neopentyl, hexyl, and the like.

Suitable "alkenyl" means straight or branched unsaturated aliphatic hydrocarbon residue having one double bond and may include lower alkenyl such as vinyl, propenyl, butenyl, methylpropenyl, pentenyl, hexenyl, and the like.

Suitable "aryl" may include phenyl, tolyl, xylyl, cumenyl, mesityl, naphthyl, and the like.

Suitable hydroxy-protective group in the "protected hydroxy" may include 1-(lower alkylthio)(lower)alkyl, trisubstituted silyl and acyl as exemplified in European Patent Publication No. 0184162, which is incorporated herein by reference.

Suitable "5- or 6-membered N-, S- or O-containing heterocyclic ring" may include pyrrolyl, tetrahydrofuryl, and the like.

Preferred embodiments of the Symbols $R^1$ to $R^{10}$, $R^{14}$ to $R^{23}$, X, Y, and n are as follows.

$R^1$ and $R^2$ are each hydrogen or combined to form a second bond;

$R^3$ and $R^4$ are combined to form a second bond;

$R^5$ and $R^6$ are combined to form a second bond;

$R^7$ is hydrogen, hydroxy, O-lower alkyl such as methoxy or protected hydroxy;

$R^8$ is hydrogen;

$R^9$ is hydroxy;

$R^{10}$ is methyl, ethyl, propyl or allyl;

$R^{14}$, $R^{15}$, $R^{16}$, $R^{17}$, $R^{18}$ and $R^{19}$ are each methyl;

$R^{20}$ is oxo or $[R^{20}a,H]$, wherein $R^{20}a$ is hydroxy or methoxy;

$R^{21}$ is $[R^{21}a,H]$, wherein $R^{21}a$ is hydroxy or protected hydroxy;

$R^{23}$ is hydrogen;

X is oxo, (H,OH) or (H,H);

Y is oxo; and n is 1 or 2.

In the above-given definitions, when a divalent group, e.g., X, is defined by an expression such as (H,OH), it is to be understood that one of the bonds to the divalent group is bonded to one of the groups contained within the parentheses, while the other bond to the divalent group is to the other group contained within the parentheses.

Particularly, the most interesting compound is FR-900506 (FK 506) of the following formula.

With respect to the macrolide compounds (I) of this invention, it is to be understood that there may be one or more conformers or stereoisomeric pairs such as optical and geometrical isomers due to asymmetric carbon atoms and double bonds, and such isomers are also included within the scope of the present invention.

Salts of the macrolide compounds of the present invention include all pharmaceutically acceptable salts without limitation.

Such macrolide compounds may be prepared by both fermentation processes and synthetic organic processes as disclosed in U.S. Pat. Nos. 4,894,366 and 4,929,611 and U.S. patent application Ser. No. 07/386,233 filed Jul. 28, 1989. These U.S. Patents and Application are incorporated herein by reference for a more complete description of the compounds having structure I, their preparation and properties.

The macrolide compounds of the present invention may be administered as pure compounds or mixtures of compounds or preferably, in a pharmaceutical vehicle or carrier.

The pharmaceutical compounds of this invention can be used in the form of a pharmaceutical preparation, for example, in solid, semisolid or liquid form, which contains the macrolide compounds of the present invention, as an active ingredient, in admixture with an organic or inorganic carrier or excipient suitable for external, enteral, intravenous, intramuscular, or parenteral applications. The active ingredient may be compounded, for example, with the usual non-toxic, pharmaceutically acceptable carriers for tablets, pellets, capsules, suppositories, solutions (saline, for example), emulsions, suspensions (olive oil, for example), and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an effective amount sufficient to produce the desired effect upon the process or condition of the disease.

Mammals with analogous diseases may be treated using the method of the present invention. Such animals may include livestock mammals such as cows, horses, etc., domestic animals such as dogs, cats, rats, etc. The present method is preferably used to treat humans.

For applying this composition to a human, it is preferable to apply it by oral, parenteral, enteral, intravenous, or intramuscular administration. Oral administration is preferred. When administered orally, the present compounds may be administered in the form of a capsule such as that described in U.S. patent application Ser. No. 07/479,465, now U.S. Pat. No. 5,196,437 which is incorporated herein by reference. While the dosage of therapeutically effective amount of the macrolide compounds varies from and also depends upon the age and condition of each individual patient to be treated, a daily dose of about 0.01–1000 mg, preferably 0.1–500 mg and more preferably 0.5–100 mg, of the active ingredient is generally given for treating pyoderma and Sezary's syndrome, and an average single dose of about 0.2–0.5 mg, 1 mg, 5 mg, 10 mg, 50 mg, 100 mg, 250 mg and 500 mg is generally administered. Daily doses for chronic administration in humans will be in the range of 0.05 mg/kg of body weight/day to 1.0 mg/kg of body weight/day, preferably 0.1 mg/kg/day to 0.6 mg/kg/day, more preferably about 0.3 mg/kg/day.

Treatment with the present compounds is effective even without the use of other drugs.

Other features of the invention will become apparent in the course of the following descriptions of exemplary embodiments which are given for illustration of the invention and are not intended to be limiting thereof.

EXAMPLES

EXAMPLE 1

Treatment of Sezary's Syndrome

Patient A had a history of Sezary's syndrome for eight and half years. She first exhibited erythroderma, pruritus and fatigue. An extensive work-up did not show any evidence of systemic involvement. She had been treated with multiple therapeutic modalities in the past including topical corticosteroids, ultraviolet irradiation, extracorporeal photospheres, high dose alpha interferon and methotrexate. For five months prior to treatment with FK506, she exhibited a marked clinical deterioration despite treatment, with progressive weight loss, fatigue and diffuse adenopathy.

Patient A was started on FK506 with a standard dose of 0.3 mg/kg/day, administered orally, in the form of a capsule. Within a week, she exhibited a dramatic response with improvement of the erythroderma and relief of her symptoms. After four weeks, a significant reduction in the size of the lymph nodes was noticed on a CT scan.

EXAMPLE 2

Treatment of Pyoderma

Patient B had a 12 year history of Chrohn's disease complicated with pyoderma gangrenosum before treatment with FK506. A subtotal colectomy was done 12 years before treatment, because of his intractable colonic lesions. The patient also had received steroid therapy with a dose of 40–70 mg/day with no significant response of his skin lesions. Patient B was started on FK506 with a dose of 0.15 mg/kg body weight p.o. bid, in the form of a capsule. The patient had an encouraging initial response within the first week. Therapy was maintained with a current oral dose of 0.30 mg/kg body weight/day with a drug blood level range of 1–1.5 mg/dL. After six months of treatment, the biochemical data did not show any evidence of renal dysfunction or disturbed lipid metabolism, and complete healing of his skin lesions was observed.

|              | Before Treatment | After Treatment (6 months) |
|---|---|---|
| BPC (mmHg)          | 110/70 | 104/64 |
| BUN (mg %)          | 14     | 19     |
| Creatinine (mg %)   | 0.5    | 1.0    |
| Cholesterol (mg %)  | 140    | 153    |
| Triglycerides (mg %)| 83     | 93     |
| Uric Acid (mg %)    | 4.0    | 4.9    |

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method for treating pyoderma, comprising administering, to a patient in need thereof, an effective amount of a compound of the formula (I)

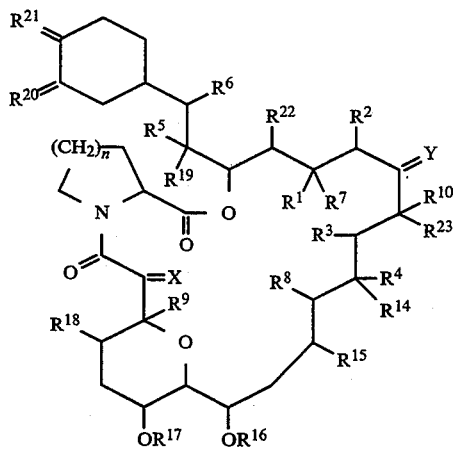

wherein each vicinal pair of substituents ($R^1$ and $R^2$), ($R^3$ and $R^4$), ($R^5$ and $R^6$) independently
a) represent two vicinal hydrogen atoms, or
b) form a second bond between the vicinal carbon atoms to which they are attached;
in addition to its significance above, $R^2$ may represent an alkyl group;
$R^7$ represents H, OH, protected hydroxy or O-alkyl, or in conjunction with $R^1$ it may represent =O;
$R^8$ and $R^9$ independently represent H or OH;
$R^{10}$ represents H, alkyl, alkyl substituted by one or more hydroxyl groups, alkenyl, alkenyl substituted by one or more hydroxyl groups, or alkyl substituted by =O;
X represents O, (H,OH), (H,H) or —$CH_2O$—;
Y represents O, (H,OH), (H,H), N—$NR^{11}R^{12}$ or N—$OR^{13}$;
$R^{11}$ and $R^{12}$ independently represent H, alkyl, aryl or tosyl;
$R^{13}$, $R^{14}$, $R^{15}$, $R^{16}$, $R^{17}$, $R^{18}$, $R^{19}$, $R^{22}$ and $R^{23}$ independently represent H or alkyl;
$R^{20}$ and $R^{21}$ independently represent O, or they may independently represent ($R^{20}$a,H) and ($R^{21}$a,H) respectively;
$R^{20}$a and $R^{21}$a independently represent OH, O-alkyl or $OCH_2OCH_2CH_2OCH_3$ or $R^{21}$a is protected hydroxy;
in addition, $R^{20}$a and $R^{21}$a may together represent an oxygen atom in an epoxide ring;
n is 1, 2 or 3;
in addition to their significances above, Y, $R^{10}$ and $R^{23}$, together with the carbon atoms to which they are attached, may represent a 5- or 6- membered N-, S- or O- containing heterocyclic ring, which may be saturated or unsaturated, and which may be substituted by one or more groups selected from alkyl, hydroxy, alkyl substituted by one or more hydroxyl groups, O-alkyl, benzyl and —$CH_2Se(C_6H_5)$;
and pharmaceutically acceptable salts thereof.

2. The method of claim 1, wherein said compound of formula (I) is FK506.

3. The method of claim 1, wherein said administering is oral administration.

4. The method of claim 1, wherein said effective amount is 0.05 mg/kg of body weight/day to 1.0 mg/kg of body weight/day.

5. A method for treating Sezary's syndrome, comprising administering, to a patient in need thereof, an effective amount of a compound of formula (I)

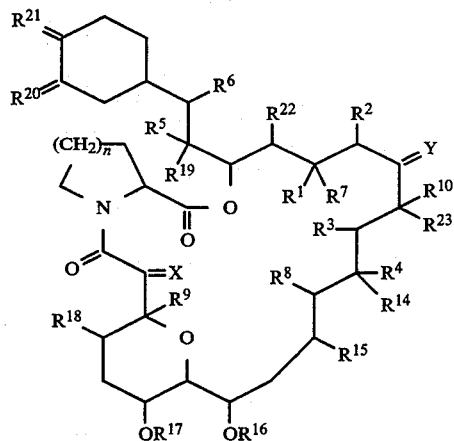

wherein each vicinal pair of substituents ($R^1$ and $R^2$), ($R^3$ and $R^4$), ($R^5$ and $R^6$) independently
a) represent two vicinal hydrogen atoms, or
b) form a second bond between the vicinal carbon atoms to which they are attached;
in addition to its significance above, $R^2$ may represent an alkyl group;
$R^7$ represents H, OH, protected hydroxy or O-alkyl, or in conjunction with $R^1$ it may represent =O;
$R^8$ and $R^9$ independently represent H or OH;
$R^{10}$ represents H, alkyl, alkyl substituted by one or more hydroxyl groups, alkenyl, alkenyl substituted by one or more hydroxyl groups, or alkyl substituted by =O;
X represents O, (H,OH), (H,H) or —$CH_2O$—;
Y represents O, (H,OH), (H,H), or N—$NR^{11}R^{12}$ or N—$OR^{13}$;
$R^{11}$ and $R^{12}$ independently represent H, alkyl, aryl or tosyl;
$R^{13}$, $R^{14}$, $R^{15}$, $R^{16}$, $R^{17}$, $R^{18}$, $R^{19}$, $R^{22}$ and $R^{23}$ independently represent H or alkyl;
$R^{20}$ and $R^{21}$ independently represent O, or they may independently represent ($R^{20}a$,H) and ($R^{21}a$,H) respectively;
$R^{20}a$ and $R^{21}a$ independently represent OH, O-alkyl or $OCH_2OCH_2CH_2OCH_3$ or $R^{21}a$ is protected hydroxy;
in addition, $R^{20}a$ and $R^{21}a$ may together represent an oxygen atom in an epoxide ring;
n is 1, 2 or 3;
in addition to their significances above, Y, $R^{10}$ and $R^{23}$, together with the carbon atoms to which they are attached, may represent a 5- or 6- membered N-, S- or O- containing heterocyclic ring, which may be saturated or unsaturated, and which may be substituted by one or more groups selected from alkyl, hydroxy, alkyl substituted by one or more hydroxyl groups, O-alkyl, benzyl and —$CH_2Se(C_6H_5)$;
and pharmaceutically acceptable salts thereof.

6. The method of claim 5, wherein said compound of formula (I) is FK506.

7. The method of claim 5, wherein said administering is oral administration.

8. The method of claim 5, wherein said effective amount is 0.05 mg/kg of body weight/day to 1.0 mg/kg of body weight/day.

9. The method of claims 1 or 5, in which said compound has the following formula:

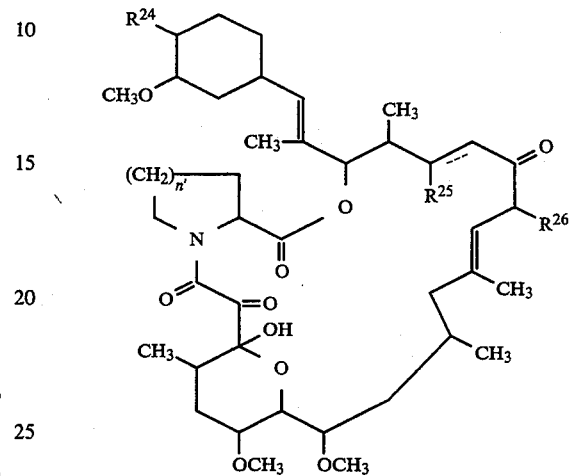

wherein
$R^{24}$ is hydroxy or protected hydroxy,
$R^{25}$ is hydrogen, hydroxy or protected hydroxy,
$R^{26}$ is methyl, ethyl, propyl or allyl,
n' is an integer of 1 or 2, and
the symbol of a line and dotted line is a single bond or a double bond,
and pharmaceutically acceptable salts thereof.

10. The method of claim 9, wherein
$R^{24}$ is hydroxy or pharmaceutically acceptable protected hydroxy selected from 1-(lower alkylthio)(-lower)-alkyloxy, tri(lower)alkylsilyloxy, lower alkyldiphenylsilyloxy, pharmaceutically acceptable organic carboxylic acyloxy, pharmaceutically acceptable organic sulfonic acyloxy, and pharmaceutically acceptable organic carbamic acyloxy, and
$R^{25}$ is hydrogen or the same meanings as $R^{24}$.

11. The method of claim 10, wherein
$R^{24}$ is hydroxy, $C_1$-$C_4$-alkanoyloxy which may have carboxy substituents, cyclo($C_5$-$C_6$)alkyloxy($C_1$-$C_4$)alkanoyloxy having two ($C_1$-$C_4$)alkyl groups on the cycloalkyl moiety, camphorsulfonyloxy, carboxy($C_1$-$C_4$)alkylcarbamoyloxy, tri($C_1$-$C_4$)alkylsilyl($C_1$-$C_4$)alkoxycarbonyl($C_1$-$C_4$)alkylcarbamoyloxy, benzoyloxy which may have one or two nitro substituents, benzenesulfonyloxy having halogen substituents, or phenyl($C_1$-$C_4$)alkanoyloxy having $C_1$-$C_4$alkoxy and trihalo($C_1$-$C_4$)alkyl substituents, and
$R^{25}$ is hydrogen, hydroxy or $C_1$-$C_4$alkanoyloxy.

12. The method of claim 11, wherein n' is an integer of 2.

13. The method of claim 12, wherein the symbol of a line and dotted line is a single bond.

14. The method of claim 13, wherein $R^{24}$ and $R^{25}$ are each hydroxy.

15. The method of claims 1 or 5, wherein said administering is external administration.

* * * * *